(12) United States Patent
Brodkin et al.

(10) Patent No.: US 6,517,623 B1
(45) Date of Patent: *Feb. 11, 2003

(54) LITHIUM DISILICATE GLASS CERAMICS

(75) Inventors: Dmitri Brodkin, West Orange, NJ (US); Carlino Panzera, Bellemead, NJ (US); Paul Panzera, Mt. Holly, NJ (US)

(73) Assignee: Jeneric/Pentron, Inc., Wallingford, CT (US)

( * ) Notice: Subject to any disclaimer, the term of this patent is extended or adjusted under 35 U.S.C. 154(b) by 76 days.

This patent is subject to a terminal disclaimer.

(21) Appl. No.: 09/640,941

(22) Filed: Aug. 17, 2000

Related U.S. Application Data

(63) Continuation-in-part of application No. 09/458,919, filed on Dec. 10, 1999, now Pat. No. 6,455,451.
(60) Provisional application No. 60/153,916, filed on Sep. 14, 1999, provisional application No. 60/122,558, filed on Mar. 2, 1999, and provisional application No. 60/111,872, filed on Dec. 11, 1998.

(51) Int. Cl.[7] .................. C03B 27/012; C03B 32/00; A61C 13/00
(52) U.S. Cl. ............... 106/35; 501/5; 433/201.1; 433/202.2; 433/212.1; 264/16; 264/19
(58) Field of Search .............. 264/16, 19; 501/5; 106/35; 433/201.1, 202.2, 212.1

(56) References Cited

U.S. PATENT DOCUMENTS

| | | |
|---|---|---|
| 2,106,744 A | 2/1938 | Hood |
| 2,515,940 A | 7/1950 | Stookey |

(List continued on next page.)

FOREIGN PATENT DOCUMENTS

| | | |
|---|---|---|
| CA | 696415 | 10/1964 |
| CA | 799407 | 11/1968 |

(List continued on next page.)

OTHER PUBLICATIONS

International Search Report Dated Apr. 8, 2000.
McMillan, P.W., Glass–Ceramics, Academic Press, Second Addition, 1979, pb 169 & 171.

(List continued on next page.)

Primary Examiner—C. Melissa Koslow
(74) Attorney, Agent, or Firm—Ann M. Knab

(57) ABSTRACT

This invention is directed to lithium disilicate ($Li_2Si_2O_5$) based glass-ceramics comprising silica, lithium oxide, alumina, potassium oxide and phosphorus pentoxide. The glass-ceramics are useful in the fabrication of single and multi-unit dental restorations (e.g. anterior bridges) made by heat pressing into refractory investment molds produced using lost wax techniques. The glass-ceramics have good pressability, i.e., the ability to be formed into dental articles by heat-pressing using commercially available equipment. In accordance with one embodiment directed to the process of making the glass-ceramics, the compositions herein are melted at about 1200° to about 1600° C., thereafter quenched (e.g., water quenched or roller quenched) or cast into steel molds, or alternately, cooled to the crystallization temperature. The resulting glass is heat-treated to form a glass-ceramic via a one or two step heat-treatment cycle preferably in the temperature range of about 400° to about 1100° C. The resulting glass ceramics are then pulverized into powder and used to form pressable pellets and/or blanks of desired shapes, sizes and structures which are later pressed into dental restorations. Alternatively, instead of forming into pressable pellets or blanks, the pulverized powder is used to form a dental restoration using the refractory die technique or platinum foil technique.

33 Claims, 1 Drawing Sheet

U.S. PATENT DOCUMENTS

| | | |
|---|---|---|
| 2,628,160 A | 2/1953 | Stookey |
| 2,684,911 A | 7/1954 | Stookey |
| 2,799,136 A | 1/1957 | Stookey |
| 2,920,971 A | 1/1960 | Stookey |
| 2,971,853 A | 2/1961 | Stookey |
| 3,006,775 A | 10/1961 | Chen |
| 3,013,362 A | 12/1961 | Calkins |
| 3,032,429 A | 5/1962 | Arthur |
| 3,114,646 A | 12/1963 | Currie |
| 3,130,061 A | 4/1964 | McMahon |
| 3,157,522 A | 11/1964 | Stookey |
| 3,170,805 A | 2/1965 | McMillan |
| 3,231,456 A | 1/1966 | McMillan |
| 3,236,610 A | 2/1966 | McMillan |
| 3,238,085 A | 3/1966 | Hayami |
| 3,252,811 A | 5/1966 | Beall |
| 3,253,975 A | 5/1966 | Olcott |
| 3,380,828 A | 4/1968 | Sack |
| 3,397,076 A | 8/1968 | Little |
| 3,436,109 A | 4/1969 | Loose |
| 3,450,546 A | 6/1969 | Stong |
| 3,458,330 A | 7/1969 | Tryggve |
| 3,460,987 A | 8/1969 | McMillan |
| 3,463,646 A | 8/1969 | Little |
| 3,499,787 A | 3/1970 | Inoue |
| 3,511,681 A | 5/1970 | Huey |
| 3,537,868 A | 11/1970 | Kosaka |
| 3,561,984 A | 2/1971 | Eppler |
| 3,564,587 A | 2/1971 | Ellis |
| 3,600,204 A | 8/1971 | Beall |
| 3,647,489 A | 3/1972 | McMillan |
| 3,650,817 A | 3/1972 | Motoyuki |
| 3,663,193 A | 5/1972 | Wilson |
| 3,804,608 A | 4/1974 | Hcoley |
| 3,809,543 A | 5/1974 | Gaskell |
| 3,816,704 A * | 6/1974 | Borom et al. .......... 219/455.12 |
| 3,907,577 A | 9/1975 | Kiefer |
| 3,929,494 A | 12/1975 | Veres |
| 3,931,438 A | 1/1976 | Beall |
| 3,939,295 A | 2/1976 | Robertson |
| 3,977,857 A | 8/1976 | Mattox |
| 4,097,295 A | 6/1978 | Chyung |
| 4,125,651 A | 11/1978 | Campbell |
| 4,186,021 A | 1/1980 | Chyung |
| 4,189,325 A | 2/1980 | Barrett |
| 4,196,004 A | 4/1980 | Berretz |
| 4,222,760 A | 9/1980 | Chyung |
| 4,289,538 A | 9/1981 | Orso |
| 4,340,645 A | 7/1982 | Oconnor |
| 4,391,914 A | 7/1983 | Beall |
| 4,414,282 A | 11/1983 | McCollister |
| 4,431,451 A | 2/1984 | Mabie |
| 4,473,653 A | 9/1984 | Rudoi |
| 4,480,044 A | 10/1984 | McAlinn |
| 4,515,634 A | 5/1985 | Wu |
| 4,672,152 A | 6/1987 | Shinobara |
| 5,030,392 A | 7/1991 | Grossman |
| 5,176,961 A | 1/1993 | Crooker |
| 5,200,369 A | 4/1993 | Clifford |
| 5,219,799 A | 6/1993 | Beall |
| 5,232,878 A | 8/1993 | Kasuga |
| 5,308,391 A | 5/1994 | Komma |
| 5,308,803 A | 5/1994 | Clifford |
| 5,330,939 A | 7/1994 | Marazzi |
| 5,466,285 A | 11/1995 | Kamiya |
| 5,507,981 A * | 4/1996 | Petticrew .................... 264/16 |
| 5,552,350 A | 9/1996 | Hornor |
| 5,567,217 A | 10/1996 | Goto |
| 5,580,363 A | 12/1996 | Goto |
| 5,702,514 A | 12/1997 | Petticrew |
| 5,744,208 A | 4/1998 | Beall |
| 5,820,989 A | 10/1998 | Reed |
| 5,847,649 A | 12/1998 | Poole |
| 5,872,069 A | 2/1999 | Abe |
| 5,874,376 A | 2/1999 | Taguchi |
| 5,895,719 A | 4/1999 | Fyles |
| 5,897,885 A | 4/1999 | Petticrew |
| 5,968,856 A * | 10/1999 | Schweiger et al. .......... 106/35 |
| 5,997,977 A | 12/1999 | Zou |
| 6,121,175 A | 9/2000 | Drescher |
| 6,174,168 B1 | 1/2001 | Dehoff |
| 6,190,171 B1 | 2/2001 | Hajjar |

FOREIGN PATENT DOCUMENTS

| | | |
|---|---|---|
| CA | 1120960 | 3/1982 |
| CA | 2213390 | 8/1997 |
| DE | 1421886 | 12/1961 |
| DE | 940706 | 10/1963 |
| DE | 2313347 | 3/1973 |
| DE | 2314722 | 3/1973 |
| DE | 2314721 | 10/1973 |
| DE | 2451121 | 10/1974 |
| DE | 3039930 | 10/1980 |
| DE | 4020893 | 6/1990 |
| EP | 0536479 | 4/1993 |
| EP | 0536572 | 4/1993 |
| EP | 0695726 | 2/1996 |
| EP | 0781731 | 2/1997 |
| EP | 0827941 | 3/1999 |
| EP | 0916625 | 5/1999 |
| FR | 2655264 | 12/1989 |
| GB | 924996 | 6/1959 |
| GB | 943599 | 12/1963 |
| GB | 955437 | 4/1964 |
| GB | 1136501 | 12/1968 |
| GB | 1312700 | 4/1973 |
| GB | 1467459 | 3/1977 |
| JP | 50-94016 | 12/1973 |
| JP | 49128011 | 12/1974 |
| JP | 62072547 | 3/1987 |
| JP | 1-145348 * | 6/1989 |
| JP | 03271130 | 3/1991 |
| JP | 10-188260 | 7/1998 |

OTHER PUBLICATIONS

Anusavice, K.J., Zhang, N.Z., Moorehead, J.E., Influence of P2O5, AgNo3 and FeCl3 on color and translucency of lithia–based glass–ceramics, Dental Materials, Jul. 1994, pp. 230–235.

Borom, M.P., Turkalo, A.M., Strength and Microstructurie in Lithium Disilicate Glass–Ceramics, Journal of the American Ceramic Society, vol. 58, 1975, p. 385–391.

Doremus, R.H. Turkalo, A.M., Crystallisation of lithium disilicate in lithium silicate glasses, Physics and Chemistry of Glasses, vol. 13, Feb. 1, 1972, p. 14–18.

Matsusita, K. Maki, T., Tashiro, M., Effect of added oxides on the crystallisation of phase separation of $Li_2O$, $3SiO_2$ glasses, Physics and Chemistry of Glasses, vol. 15, No. 4, Aug. 1974, p. 106–108.

Ridone, G.E, Influence of Platinum Nucleation on Crystallization of a Lithium Silicate Glass, Journal of the American Ceramic Society–Discussion and Notes, vol. 41, 1958, p. 41–42.

Ridone, G.E., Further Studies of Crystallization of a Lithium Silicate Glass, Journal of the American Ceramic Society, vol. 45, 1962, p. 7–12.

Sorenson, J.A., Cruz, M., Mito, W.T, Raffeiner, O., Meredity, H.R., Foser, H.P., A Clinical Investigation on Three–Unit Fixed Partial Dentures Fabricated with a Lithium Disilicate Glass–Ceramic. Practical Periodontics & Aesthetic Dentistry, 1998, 11(1) p. 95–107.

Barrett, J.M., Chemical and Physical Properties of Multicomponent Glasses and Glass Ceramics. A Thesis presented to the Graduate Council of the Univeristy of Florida in Partial Fulfillment of the Requirement for the Degree of Master of Science, University of Florida, 1978.

Faber, K.T., Evans, A.G., Crack Deflection Processes II., Experiment, Acta Metall, 31, 4, pp. 577–584, 1983.

Dillmore, M.F., Clark, D.E., Hench, L.L., Corrosion Behavior of Lithia Disilicate Glass in Aqueous Solutions of Aluminum Compounds. Ceramic Bulliten, p. 1111–1124. vol. 58., No. 11 (1979).

Freiman, S.W., Hench. L.L., Effect of Crystallization on the Mechanical Properties of Li2O–SiO2 Glass–Ceramics. Journal of the American Ceramic Society, p. 86–90, vol., 55, No. 2.

McCracken, W.J., Clark, D.E., Hench, L.L., Aqueous Durability of Lithium Disilicate Glass–Ceramics, Ceramic Bulliten, p. 1218–1223, vol. 61. No. 11 (1982).

McCracken, J.W., Person, W.B., Hench, L.L., Polarized infared relfection spectroscopy of single crystal lithia–silicates and quartz. Journal of Materials Science. p. 3853–3864. 20. 1985.

Ohuchi, F. Clark, D.E., Hench. L.L., Effect of Crystallization on the Auger Election Signal Decay in an Li2O 2SiO2 Glass and Glass–Ceramic. Journal of the American Ceramic Society. p. 500–503. Sep.–Oct. 1979.

Palmer, R.A. Lindberg. W.R., Hench. L.L., Fatigue Properties of Li2O 2SiO2 Glass and Glass Ceramic. Journal of the American Ceramic Society—Discussion and Notes. p. 319–320. vol. 62, No. 5–6, May–Jun. 1979.

Hench, L.L., S.W. Frieman & Kinser, D.L., The Early Stages of Crystallisation in a Li2O–2SiO2 Glass, Physics and Chemistry of Glasses vol. 12, No. 2, Apr. 1971.

* cited by examiner

LITHIUM DISILICATE GLASS CERAMICS

CROSS-REFERENCE TO RELATED APPLICATIONS

This application is a continuation-in-part of U.S. application Ser. No. 09/458,919, filed Dec. 10, 1999, now U.S. Pat. No. 6,455,451, which claims priority to U.S. Provisional Application No. 60/153,916, filed Sep. 14, 1999, U.S. Provisional Application No. 60/122,558, filed Mar. 2, 1999, and U.S. Provisional Application No. 60/111,872, filed Dec. 11, 1998, all which are incorporated herein by reference.

FIELD OF INVENTION

This invention relates generally to glass-ceramics comprising lithium disilicate and more specifically to glass-ceramics for use in the manufacture of dental restorations and methods of manufacture thereof.

BACKGROUND OF THE INVENTION

The use of lithium disilicate glass ceramics for use in dental restorations has been suggested in the prior art. U.S. Pat. No. 4,189,325 to Barret et al. is directed to a glass-ceramic comprising lithium disilicate for use in dental restorations. The glass ceramic requires the presence of $Nb_2O_5$ and Pt as nucleation agents. Barrett et al. introduced dental restorations made from castable lithium disilicate glass-ceramics in the $Li_2O$-$CaO$-$Al_2O_3$-$SiO_2$ system nucleated by Pt and $Nb_2O_5$. According to Barret et al., dental restorations are made by casting a melt into an investment mold, and devitrifying thereafter.

U.S. Pat. No. 4,515,634 to Wu et al. is directed to a castable glass-ceramic composition wherein the glass is melted and cast into a shape and is crystallized after it has been shaped. Therefore, the crystallization process is performed by the technician making the restoration, not the manufacturer of the dental material. Wu set al. suggests one way to improve properties of castable lithium disilicate dental restorations within the same $Li_2O$-$CaO$-$Al_2O_3$-$SiO_2$ system as described by Barrett et al. is by utilization of $P_2O_5$ as a nucleating agent. Both Barrett et al. and Wu et al. describe castable compositions having CaO as an essential ingredient believed to improve chemical durability of the resulting glass-ceramics. Chemical durability is one of the major issues that the Wu and Barrett inventions fail to address. For example, total alkali leaching rates for materials presented in Wu's examples were four to five times higher than those for commercial dental porcelain.

Castable dental ceramics as described in Barret et al. and Wu et al. employ melting glass ingots supplied by a manufacturer and casting dental articles into a refractory investment mold. Following the casting process, the cast articles are devitrified (crystallized) by the required heat-treatment steps. This process is very similar to casting metals whereby a heat-treatment step follows the casting process to increase hardness and strength.

U.S. Pat. Nos. 5,507,981 and 5,702,514 to Petticrew teach lithium disilicate compositions for use in dental restorations, but the method described therein implies forming glass into the shape of a dental restoration at temperatures much higher than the melting temperature of lithium disilicate and heat-treating the dental restoration after forming to convert the glass into a glass-ceramic.

German Patent Application No. DE19647739 to Schweiger et al. is directed to lithium disilicate compositions for use in dental restorations. The glass-ceramic bodies or blanks used to press dental restorations are defined as "sinterable glass ceramics" which are produced from the starting amorphous glass powder by simultaneous sintering and powder crystallizing, which process is also known as surface crystallization. The glass must be in powder form to be crystallized. Additionally, the lithium disilicate compositions therein require the presence of $La_2O_3$, MgO and ZnO.

Many of the lithium disilicate compositions in the prior art require casting of the glass into the desired shape and crystallizing thereafter. The glass must be formed into the finally desired shape and thereafter heat treated to crystallize into a lithium disilicate phase. This may result in structural and other problems, since the microstructure is not formed by the dental materials manufacturer, but by the technician fabricating the dental restoration. Overprocessing by a technician may change the microstructure of the material to something not preferred or desired by the dental materials manufacturer. Moreover, some of the prior art compositions require the forming of the glass ceramics by surface crystallization, limiting the forming and compositional possibilities of the material.

It is desirable to provide a lithium disilicate glass-ceramic which is pressable or formable after the lithium disilicate is formed. It is beneficial to provide a lithium disilicate glass ceramic for use in the fabrication of dental restorations wherein crystallization is carried out by the dental materials manufacturer in the most controlled manner. It is beneficial to provide translucent lithium disilicate glass ceramics having high strength and good presssability.

SUMMARY OF THE INVENTION

This invention is directed to lithium disilicate ($Li_2Si_2O_5$) based glass-ceramics comprising silica, lithium oxide, alumina, potassium oxide and phosphorus pentoxide in addition to other components listed below. The glass-ceramics are useful in the fabrication of single and multi-unit dental restorations including but not limited to orthodontic appliances, bridges, space maintainers, tooth replacement appliances, splints, crowns, partial crowns, dentures, posts, teeth, jackets, inlays, onlays, facing, veneers, facets, implants, abutments, cylinders, and connectors made by a variety of techniques including heat pressing into refractory investment molds produced using lost wax techniques or building and sintering powder onto refractory dies such as in the refractory die/foil technique. The glass-ceramics have good pressability, i.e., the ability to be formed into dental articles by heat pressing, also known as hot pressing, or injection molding, using commercially available equipment and good formability, i.e., the ability to be applied in powder form to a dental model, i.e., on a refractory die, and heated to form a dental restoration.

In accordance with one embodiment directed to the process of making the glass-ceramics, the compositions herein are melted at about 1200° to about 1600° C. and preferably in the range of about 1300° to about 1400° C. for a period of time, preferably for about 4 hours and thereafter quenched (e.g., water quenched or roller quenched) or cast into steel molds, or alternately, cooled to the crystallization temperature.

The resulting glass is heat-treated to form a glass-ceramic via a one or two step heat-treatment cycle preferably in the temperature range of about 400° to about 1100° C. This crystallization heat treatment may comprise a nucleation step and a crystal growth step. Depending on the composition, the first, nucleation step, may be carried out in the range of about 450° C. to about 700° C. and preferably in the range of about 500° C. to about 650° C. for about 0.5 to about 4 hours and the second, crystal growth step, may be carried out in the range of about 800° C. to about 1000° C. and preferably in the range of about 830° C. to about 930° C. for about 0.5 to about 48 hours. The most preferable heat treatment comprises about a one hour soak at about 645° C. and a subsequent four hour soak at about 850° C.

The resulting glass ceramics are then pulverized into powder and used to form pressable pellets and/or blanks of desired shapes, sizes and structures. Additives may be mixed with the powder prior to forming into pellets or blanks. These pellets and blanks may be used for pressing cores or other frameworks or shapes for dental restorations. The blank or pellet may be subjected to viscous deformation at a temperature in the range of about 800° to about 1200° C., and more preferably in the range of about 850° to about 950° C., and most preferably at less than about 930° C., under vacuum and with the application of pressure of between about 2 to about 8 bar (0.2 to 0.8 MPa) and preferably no greater than about 6 bar (0.6 MPa) to obtain a dental restoration. Moreover, it is possible that the blanks may be machined to a dental restoration of desired geometry.

Alternatively, instead of forming into pressable pellets or blanks, the pulverized powder, with or without additives, is used to form a dental restoration using the refractory die technique or platinum foil technique.

BRIEF DESCRIPTION OF THE DRAWINGS

Features of the present invention are disclosed in the accompanying drawing, wherein.

DESCRIPTION OF THE INVENTION

Figure 1:
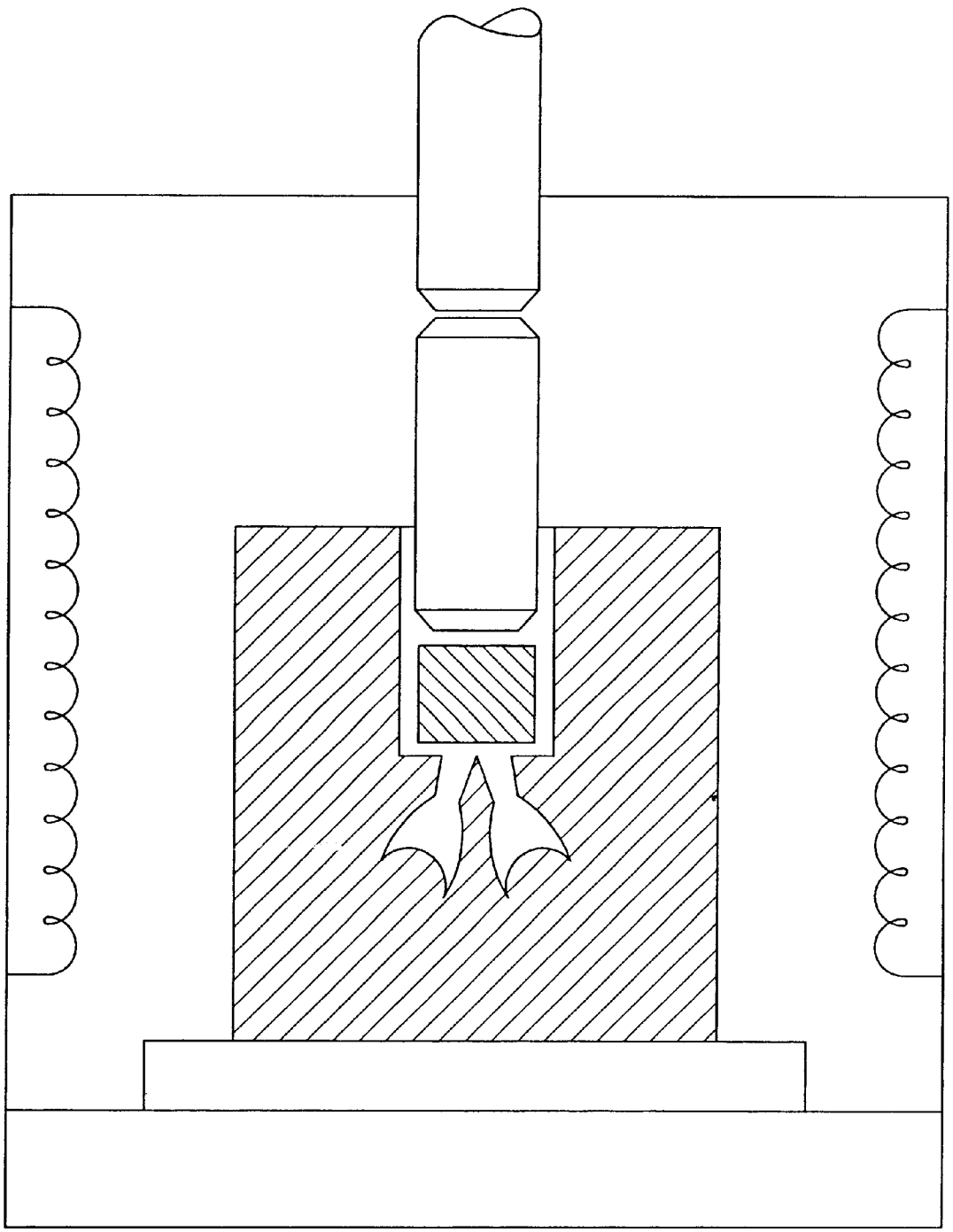
FIG. 1 s perspective view of a plunger system in a pressing furnace for use in the fabrication of dental restorations in accordance with one embodiment of the invention.

As will be appreciated, the present invention provides glass-ceramic compositions comprising a glassy matrix and lithium disilicate ($Li_2Si_2O_5$). The glass-ceramics are useful for the fabrication of dental restorations. The compositions of the lithium disilicate glass-ceramics comprise inter alia, silica, lithium oxide, alumina, potassium oxide and phosphorus pentoxide in the ranges given in Table 1 below. The glass-ceramic compositions of the invention have a combination of properties useful for dental restorations. The glass-ceramics have good pressability, i.e., the ability to be formed into dental articles by heat pressing, also known as hot pressing, or injection molding, using commercially available equipment. The glass-ceramics also have good formability, i.e., the ability to be applied in powder form to a dental model and heated to form a dental restoration.

Pressable ceramics employ some form of hot-pressing or injection-molding of the glass-ceramic materials, which are typically in the form of pellets. The pellets contain one or more crystalline phases and their morphology as well as volume fraction are not significantly altered in the course of pressing. One reason for this is that the pressing temperature is typically lower than the melting temperature of the crystalline phases. This is a major advantage because microstructure is formed in the controlled conditions by the manufacturer of the glass-ceramic materials, e.g., pellets. Following pressing, the resulting dental article does not require crystallization heat-treatment. Similarly, the powder glass-ceramics contain one or more crystalline phases and their morphology and volume fraction are not significantly altered in the course of sintering during the fabrication of a dental article.

The glass-ceramic pellets can be formed by a number of processes: (1) Glass can be cast into the shape of pellet. Pellets are taken from the mold and crystallized. These pellets can not be shaded by the addition of pigments. (2) Glass can be crystallized in bulk and subsequently milled into powder. Pigments and other additives can be added to the powder. The powder is formed into a pellet and partially or fully sintered. Pigments, if added, create color centers that impart a certain color to a translucent body of the dental article pressed from the pellet. The mechanism of crystallization in the two processes described above is volume crystallization. Volume crystallization as described in process two above may be used to form glass-ceramic powder without forming into a pellet.

Alternatively, surface crystallization may be utilized to crystallize a portion of the glass into one or more crystal phases. This involves milling glass into powder. Pigments and other additives can be added to the powder. This glass powder (amorphous, not crystalline) is formed into a pellet. The glass pellet is sintered and crystallized in the same firing cycle. Not all glass-ceramic materials can be crystallized and sintered simultaneously. Only certain materials and compositions prone to surface crystallization can be processed this way. The glass-ceramics processed from glass powder via simultaneous sintering and crystallization are sometimes called "sintered" glass-ceramics. Another term that can be used is "sinterable" glass-ceramics.

The compositions herein are prepared by mixing, in the desired proportions, the oxides and/or compounds that decompose to form the oxides, followed by fusing the ingredients to obtain the compositions in Table 1. Convenient raw material include lithium carbonate, silica, alumina, carbonates of K, Na, Ca, ammonium phosphate, tricalcium aluminate, aluminum phosphate or aluminum metaphosphate and if necessary, $Ta_2O_5$, $CeO_2$, $Tb_4O_7$, titanium dioxide, and zirconium dioxide.

TABLE 1

| Oxide, wt % | Range 1 | Range 2 | Range 3 | Range 4 | Range 5 | Range 6 |
|---|---|---|---|---|---|---|
| $SiO_2$ | about 62 to about 85 | about 64 to about 70 | about 62 to about 85 | about 64 to about 70 | About 64 to about 70 | about 62 to about 76 |
| $B_2O_3$ | 0 to about 4.9 | 0 -to about 2.7 | 0 to about 4.9 | 0 to about 2.7 | 0.5 to about 3.0 | 0 to about 5 |
| $Al_2O_3$ | about 1.5 to about 10 | about 1.5 to about 6.0 | about 5.1 to about 10 | about 5.2 to about 9.0 | about 1.5 to about 6.0 | about 1.5 to about 10 |
| F | 0 to about 1.5 | 0 to about 1.5 | 0 to about 1.5 | 0 to about 1.5 | 0 to about 1.5 | 0 to about 1.5 |
| ZnO | 0 to about 5 | 0 to about 2 | 0 to about 5 | 0 to about 2 | — | 0 to about 5 |
| CaO | 0 to about 7 | 0 to about 0.9 | 0 to about 7 | 0 to about 0.9 | 0 to about 0.9 | 0 to about 7 |
| MgO | 0 to about 2 | 0 to about 2 | 0 to about 2 | 0 to about 2 | — | 0 to about 2 |

TABLE 1-continued

| Oxide, wt % | Range 1 | Range 2 | Range 3 | Range 4 | Range 5 | Range 6 |
|---|---|---|---|---|---|---|
| BaO | 0 to about 7 | 0 to about 7 | 0 to about 7 | 0 to about 7 | 0 to about 7 | 0 to about 7 |
| SrO | 0 to about 1 | 0 to about 1 | 0 to about 1 | 0 to about 1 | 0 to about 1 | 0 to about 1 |
| $Cs_2O$ | 0 to about 5 | 0 to about 5 | 0 to about 5 | 0 to about 5 | 0 to about 5 | 0 to about 5 |
| $Li_2O$ | about 8 to about 19 | about 10 to about 15 | about 8 to about 19 | about 10 to about 15 | about 10 to about 15 | about 8 to about 19 |
| $K_2O$ | about 2.5 to about 7 | about 2.5 to about 5 | 0 to about 7 | 0 to about 5 | about 2.2 to about 5 | 0 to about 7 |
| $Na_2O$ | 0 to about 5 | 0 to about 3 | 0 to about 5 | 0 to about 3 | about 0.5 to about 3 | 0 to about 5 |
| $TiO_2$ | 0 to about 2 | 0 to about 2 | 0 to about 2 | 0 to about 2 | 0 to about 2 | 0 to about 2 |
| $ZrO_2$ | 0 to about 3 | 0 to about 3 | 0 to about 3 | about 0 to about 3 | 0 to about 3 | 0 to about 3 |
| $P_2O_5$ | about 0.5 to about 12 | about 2 to about 7 | about 0.5 to about 12 | about 2 to about 7 | about 2 to about 7 | about 0.3 to about 7.0 |
| $SnO_2$ | 0 to about 1 | 0 to about 1 | 0 to about 1 | 0 to about 1 | 0 to about 1 | 0 to about 1 |
| $Sb_2O_3$ | 0 to about 1 | 0 to about 1 | 0 to about 1 | 0 to about 1 | 0 to about 1 | 0 to about 1 |
| $Y_2O_3$ | 0 to about 3 | 0 to about 3 | 0 to about 3 | 0 to about 3 | 0 to about 3 | 0 to about 3 |
| $CeO_2$ | 0 to about 1 | 0 to about 1 | 0 to about 1 | 0 to about 1 | 0 to about 1 | 0 to about 1 |
| $Eu_2O_3$ | 0 to about 1 | 0 to about 1 | 0 to about 1 | 0 to about 1 | 0 to about 1 | 0 to about 1 |
| $Tb_4O_7$ | 0 to about 1 | 0 to about 1 | 0 to about 1 | 0 to about 1 | 0 to about 1 | 0 to about 1 |
| $Nb_2O_5$ | 0 to about 2 | 0 to about 2 | 0 to about 2 | 0 to about 2 | 0 to about 2 | 0 to about 2 |
| $Ta_2O_5$ | 0 to about 2 | 0 to about 2 | 0 to about 2 | 0 to about 2 | 0 to about 2 | about 0.5 to about 8.0 |

For each of the compositions in Table 1, the molar ratio of $(Na_2O+K_2O+CaO+SrO+BaO)/(Al_2O_3+ZnO) \geq 1.3$. The compositions in Table 1 are melted at about 1200° to about 1600° C. and preferably in the range of about 1300° to about 1400° C. for a period of time, preferably for about 4 hours and thereafter quenched (e.g., water quenched or roller quenched), cast into steel molds, or alternately, cooled to the crystallization temperature. If the melt is cooled to the crystallization temperature, it may remain in the same furnace.

The resulting glass is heat-treated to form glass-ceramics using a one or a two step heat-treatment cycle preferably in the temperature range of about 400° to about 1100° C. This crystallization heat-treatment may comprise a nucleation step and a crystal growth step. Depending on the composition, the first, nucleation step, may be carried out in the range of about 450° C. to about 700° C. and preferably in the range of about 500° C. to about 650° C. for about 0.5 to about 4 hours and the second, crystal growth step, may be carried out in the range of about 800° C. to about 1000° C. and preferably in the range of about 830° C. to about 930° C. for about 0.5 to about 48 hours. The most preferable heat treatment comprises about a one hour soak at about 645° C. and a subsequent four hour soak at about 850° C.

The glass ceramics comprise lithium disilicate. The resulting glass ceramics are then pulverized into powder sieved to −200 mesh to provide powder with average particle sizes of about 30 to about 40 microns. Pigments, fluorescing agents, opacifying agents, and the like may be added to the powder in a wide range in an amount between about 0 and about 6 wt % and preferably in the amount of between about 0 and about 5 wt % and most preferably in the amount of about 0% to about 3 wt %. Moreover, reinforcing agents may be added to the powder in an amount of from about 0 to about 30 vol % and more preferably in an amount of from about 0 to about 20 vol %. The reinforcing agents may include fibers, whiskers, and particulate fillers and may be fabricated of any known material, preferably a glass or ceramic material.

The powders may be used in powder form to produce a dental material or may be used to form and fuse pressable pellets and/or blanks of desired shapes, sizes and structures. These pellets and blanks may be used for pressing cores or other frameworks or shapes for dental restorations. The blank or pellet may be subjected to viscous deformation at a temperature in the range of about 800° to about 1200° C., and more preferably in the range of about 850° to about 950° C., and most preferably at less than about 930° C., under vacuum and with the application of pressure of between about 2 to about 8 bar (0.2–0.8 MPa) and preferably no greater than about 6 bar (0.6 MPa) to obtain a dental restoration. Moreover, it is possible that the blanks may be machined to a dental restoration of desired geometry using commercially available milling equipment such as the Maho HGF 500 5 Axis CNC Milling Machine available from Fraunhofer Institut Produktionstechnologie, Germany. When powder is used to fabricate dental restorations, the powder is applied to the mold using refractory die techniques or the platinum foil technique. The powder is formed onto a die to form a dental restoration and is sintered.

In an alternative method herein, the compositions in Table 1 are melted at about 1200° to about 1600° C. and preferably in the range of about 1300° to about 1400° C. for a period of time, preferably for about 4 hours and thereafter water quenched or cast into steel molds.

The quenched glass is comminuted to a powder. Pigments, fluorescing agents, opacifying agents, and the like may be added to the powder in a wide range in an amount between about 0 and about 6 wt % and preferably in the amount of between about 0 and about 5 wt % and most preferably in the amount of about 0% to about 3 wt %. Moreover, reinforcing agents may be added to the powder in an amount of from about 0 to about 30 vol. % and more preferably in an amount of from about 0 to about 20 vol. %. The reinforcing agents may include fibers, whiskers, and particulate fillers and may be fabricated of any known material, preferably a ceramic material.

The powder is compacted into a pellet or starting blank. The blank is thereafter simultaneously sintered and crystallized. Heat treatment may be one or more cycles in the temperature range of about 400° to about 1100° C. The crystallization may comprise a nucleation step and a crystal growth step. Depending on the composition, the first, nucleation step, may be carried out in the range of about 450° C.

to about 700° C. and preferably in the range of about 500° C. to about 650° C. for about 0.5 to about 4 hours and the second, crystal growth step, may be carried out in the range of about 800° C. to about 1000° C. and preferably in the range of about 830° C. to about 930° C. for about 0.5 to about 48 hours. The most preferable heat treatment comprises about a one hour soak at about 645° C. and a subsequent four hour soak at about 850° C.

The blank or pellet may be subjected to viscous deformation at a temperature in the range of about 800° to about 1200° C., and more preferably in the range of about 850° to about 950° C., and most preferably at less than about 930° C., under vacuum and with the application of pressure of about between about 2 to about 8 bar (0.2–0.8 MPa) and preferably no greater than 6 bar (0.6 MPa) to obtain a dental restoration. Moreover, it is possible that the blanks may be machined to a dental restoration of desired geometry.

To achieve the required combination of properties, namely sufficient strength, formability below 950° C., by heat-pressing using commercially available dental presses such as the Autopress® Plus available from Jeneric/Pentron, Wallingford, Conn., translucency and chemical durability, the optimal chemical combinations and crystallization treatment of the present invention are necessary. The best properties are obtained when the lithium metasilicate ($Li_2SiO_3$) and silica phases are nearly absent, the volume fraction of $Li_3PO_4$ is less than about 5% and the volume fraction of lithium disilicate ($Li_2Si_2O_5$) is between about 35% and about 60%. High aspect ratio morphology of the lithium disilicate phase is important and is believed to enhance mechanical properties, i.e., strength and fracture toughness of the glass-ceramic.

$Li_2O$ and $SiO_2$ are instrumental in crystallizing the required amount of the lithium dislicate phase in the compositions of the present invention. Additionally, BaO and $Cs_2O$ stabilize the residual glass and boost the refractive index of the residual glass to match that of lithium disilicate. $Al_2O_3$ and to a lesser extent, $B_2O_3$, if less than 3%, yield chemically durable glass-ceramics that exhibit a sufficiently low solubility. Alkali (Na, K, Cs) and alkaline earth metal (Ca, Ba) oxides are required to lower processing temperatures of the glass-ceramic. However some of them affect chemical durability more than others. With respect to the following group of alkali metals and alkaline earth metals of potassium, calcium, sodium, and barium; potassium is associated with the smallest decrease in chemical durability of lithium containing glasses, with calcium being next, and sodium and barium affecting chemical durability the most. However, the best combination of properties is achieved when those oxides are used in combination to achieve the so-called "mixed alkali effect." F lowers the viscosity of the glass-matrix and enhances formability at temperatures below about 950° C. $Y_2O_3$ in combination with $Ce_2O_3$, $Eu_2O_3$ and $Tb_4O_7$ modify the refractive index as well as impart fluorescence. $Nb_2O_5$ and $Ta_2O_5$ modify the refractive index as well as aid nucleation and chemical durability of the resulting glass ceramics.

The following Table 2 illustrates examples of the compositions of the invention.

TABLE 2

| Oxide, wt % | Ex. 1 | Ex. 2 | Ex. 3 | Ex. 4 | Ex. 5 | Ex. 6 | Ex. 7 | Ex. 8 | Ex. 9 | Ex. 10 |
|---|---|---|---|---|---|---|---|---|---|---|
| $SiO_2$ | 68.8 | 70.0 | 70.1 | 68.1 | 69.5 | 68.8 | 65 | 67.2 | 68.9 | 72 |
| $B_2O_3$ | 1.2 | 1.0 | — | — | 1.3 | 1.3 | 1.0 | 1.2 | 0.9 | 2.0 |
| $Al_2O_3$ | 4.8 | 4.9 | 5.2 | 4.7 | 4.8 | 4.8 | 5 | 4.7 | 47 | 4.5 |
| F | — | — | — | — | — | — | — | — | — | — |
| ZnO | — | — | — | — | — | — | — | — | — | — |
| CaO | 0.9 | 0.5 | 2.2 | 2.0 | 2.0 | 1.0 | 1 | 1 | 0.5 | 0 |
| MgO | — | — | — | — | — | — | — | — | — | — |
| BaO | 2.8 | 1.4 | — | — | — | 2.8 | 2.7 | 2.7 | 1.4 | 2.0 |
| SrO | — | — | — | — | — | — | — | — | — | — |
| $Cs_2O$ | — | — | — | — | — | — | — | — | — | — |
| $Li_2O$ | 14.4 | 14.7 | 14.7 | 14.3 | 14.6 | 14.4 | 15 | 14.1 | 14.3 | 13.0 |
| $K_2O$ | 2.5 | 2.5 | 4.6 | 4.4 | 4.5 | 2.2 | 2.2 | 2.2 | 2.0 | 2.0 |
| $Na_2O$ | 1.4 | 1.4 | — | — | — | 1.5 | 1.4 | 1.4 | 1.3 | — |
| $TiO_2$ | — | — | — | — | — | — | — | — | — | — |
| $ZrO_2$ | — | — | — | — | — | — | — | — | — | — |
| $P_2O_5$ | 3.3 | 3.6 | 3.4 | 3.3 | 3.4 | 3.3 | 3.5 | 3.2 | 3.5 | 3.0 |
| $SnO_2$ | — | — | — | — | — | — | — | — | — | — |
| $Sb_2O_3$ | — | — | — | — | — | — | — | — | — | — |
| $Y_2O_3$ | — | — | — | — | — | — | — | — | — | 0.5 |
| $CeO_2$ | — | — | — | 0.4 | — | — | 0.4 | 0.4 | 0.3 | 0.6 |
| $Eu_2O_3$ | — | — | — | — | — | — | — | — | — | 0.6 |
| $Tb_4O_7$ | — | — | — | 0.8 | — | — | 0.9 | — | 0.3 | — |
| $Nb_2O_5$ | — | — | — | — | — | — | — | — | — | — |
| $Ta_2O_5$ | — | — | — | 2.0 | — | — | 1.9 | 2.0 | 1.8 | — |
| Molar ratio of ($Na_2O$ + $K_2O$ + CaO + SrO + BaO): (ZnO + $Al_2O_3$) | 1.772 | 1.398 | 1.727 | 1.787 | 1.772 | 1.777 | 1.66 | 1.765 | 1.307 | 0.777 |
| Three-Point Flexural Strength per ISO 6872, MPa | | | | | | 420 ± 60 | | 440 ± 60 | | 400 ± 50 |

TABLE 2-continued

| Oxide, wt % | Ex. 1 | Ex. 2 | Ex. 3 | Ex. 4 | Ex. 5 | Ex. 6 | Ex. 7 | Ex. 8 | Ex. 9 | Ex. 10 |
|---|---|---|---|---|---|---|---|---|---|---|
| As-pressed Opacity (relative opacity units) | | | | | | 42 | | 25 | | 34 |
| CTE (25° C.–500° C.), $10^{-6}$ °C.$^{-1}$ | | 10.4 | | | | 10.1–10.6 | | 10.5 | 10.0 | 9.9 |

The following examples illustrate the invention.

EXAMPLE 1

Glass-ceramic compositions of the present invention were utilized to make glass-ceramic pellets. These pellets were used to make rectangular bars and rods for measuring the flexural strength by heat-pressing these pellets into the cavity of the refractory investment mold. The process was the same as that used to make dental restorations. The three-point flexure strength was greater or equal to 300 MPa. This strength is sufficient for multi-unit restorations such as anterior bridges. The compositions have a significant amount of glass phase, i.e., approximately 50% glass phase which enhances the pressability thereof.

Moreover, the closeness of refractive indices of the matrix glass (~1.5) and that of the crystallized phase—lithium disilicate—(~1.55) allows for the possibility of translucent glass-ceramics. Specifically in the present invention, the refractive index of the glass matrix is increased to match that of the lithium disilicate phase by adding small amounts of heavy ions such as, but not limited to, Sr, Y, Nb, Cs, Ba, Ta, Ce, Eu and Tb.

The following examples in Table 3 illustrate the effect of different additions on translucency, strength and reactivity with investment of the resulting glass ceramics. The composition of Example 6 (Table 2) was selected as a control composition for the purposes of this study. This composition was modified by adding 0.13 mole% of $CeO_2$, or 0.06 mole% of $Tb_4O_7$, or 0.26 mole% of $Ta_2O_5$, or $La_2O_3$, or $Y_2O_3$; and combinations of the latter with $CeO_2$. Opacity was measured on the pressed disk using an optical densitometer. Reactivity with investment was evaluated qualitatively by visual inspection of disks and copings prior to and after sand-blasting of the reaction layer. Surfaces of the disks were inspected for pittings under low-magnification (8x) stereomicroscope. Compositions comprising combinations of $Ta_2O_5$, and $CeO_2$ were found to have the best combination of high translucency (low opacity) and low reactivity with the investment.

TABLE 3

| Oxide, wt % | Ex. 6* | Ex. 16 | Ex. 17 | Ex. 18 | Ex. 19 | Ex. 20 | Ex. 21 | Ex. 22 | Ex. 8* | Ex. 23 |
|---|---|---|---|---|---|---|---|---|---|---|
| $SiO_2$ | 68.8 | 68.12 | 68.5 | 68.2 | 67.5 | 67.8 | 67.9 | 68.0 | 67.2 | 67.5 |
| $B_2O_3$ | 1.3 | 1.2 | 1.2 | 1.2 | 1.2 | 1.2 | 1.2 | 1.2 | 1.2 | 1.2 |
| $Al_2O_3$ | 4.8 | 4.7 | 4.8 | 4.7 | 4.7 | 4.7 | 4.7 | 4.7 | 4.7 | 4.7 |
| CaO | 1.0 | 1.0 | 1.0 | 1.0 | 1.0 | 1.0 | 1.0 | 1.0 | 1.0 | 1.0 |
| BaO | 2.8 | 2.7 | 2.8 | 2.7 | 2.7 | 2.7 | 2.7 | 2.7 | 2.7 | 2.7 |
| $Li_2O$ | 14.4 | 14.3 | 14.3 | 14.3 | 14.1 | 14.2 | 14.2 | 14.2 | 14.1 | 14.1 |
| $K_2O$ | 2.2 | 2.2 | 2.2 | 2.2 | 2.2 | 2.2 | 2.2 | 2.2 | 2.2 | 2.2 |
| $Na_2O$ | 1.5 | 1.4 | 1.5 | 1.4 | 1.4 | 1.4 | 1.4 | 1.4 | 1.4 | 1.4 |
| $P_2O_5$ | 3.3 | 3.3 | 3.3 | 3.3 | 3.3 | 3.3 | 3.3 | 3.3 | 3.2 | 3.3 |
| $Y_2O_3$ | — | 1.04 | — | — | — | — | 1.04 | — | — | — |
| $CeO_2$ | — | — | 0.39 | — | — | — | 0.39 | 0.39 | 0.39 |
| $Tb_4O_7$ | — | — | — | 0.85 | — | — | — | 0.85 | — | — |
| $Ta_2O_5$ | — | — | — | — | 2.02 | — | — | — | 2.01 | — |
| La2O3 | — | — | — | — | — | 1.5 | — | — | — | 1.49 |
| Motar ratio of ($Na_2O + K_2O + CaO + SrO + BaO$):($ZnO + Al_2O_3$) | 1.777 | 1.765 | 1.777 | 1.765 | 1.765 | 1.765 | 1.765 | 1.765 | 1.765 | 1.765 |
| 3-pt Flexure Strength per ISO 6872, MPa | 420 ± 60 | | | | | | | | 440 ± 60 | |
| As-Pressed Rod 3-pt Flexure Strength, MPa | 370 ± 40 | | | | | | | | 370 ± 30 | |
| As-pressed Opacity (relative opacity units) | 42 | 35 | 39 | 37 | 27 | 25 | 31 | 32 | 25 | 24 |

TABLE 3-continued

| Oxide, wt % | Ex. 6* | Ex. 16 | Ex. 17 | Ex. 18 | Ex. 19 | Ex. 20 | Ex. 21 | Ex. 22 | Ex. 8* | Ex. 23 |
|---|---|---|---|---|---|---|---|---|---|---|
| Reactivity with investment material | — | Medium | Lower | Higher | Medium | Higher | Lower | Medium | Lower | Highest |

*Correspond to compositions in Table 2.

Pellets of the compositions of Examples 2, 6, 8 and 9 were used to press a variety of dental articles in the AutoPress® dental press (Jeneric/Pentron, Wallingford, Conn.) at pressing cycles carried out under vacuum and involving heating from 700° C. to 920° C. and holding the temperature for 20 minutes prior to initiation of the pressing cycle. Pressure of 0.5 MPa was applied for 7 minutes through a mold-plunger assembly schematically shown in FIG. 1. The plunger assembly used to press the pellets into dental restorations may be the system set forth in copending commonly assigned application Ser. No. 09/431,659, filed Nov. 1, 1999, now U.S. Pat. No. 6,302,186, which is hereby incorporated by reference. Disks of compositions of examples 11 and 13 were pressed as described above and chemical solubility was measured according to ISO 6872 and found to be significantly lower than the acceptable limit of 100 $\mu g/cm^2$.

EXAMPLE 2

Three different powders of lithium disilicate glass-ceramics given in Table 4 below were used to make jacket crowns. One powder was formed from the composition of Example 24, a second powder was formed from fifty percent of the composition of Example 25 and fifty percent of the composition of Example 26, and a third powder was formed from the composition of Example 26. The powders were mixed with water to a thick paste consistency and were applied to refractory dies made form Polyvest Refractory Die Material available from Whip Mix Corp., Louisville, Ky. and Synvest Refractory Die Material available from Jeneric/Pentron Inc., Wallingford, Conn. Both investments were found adequate. Cores were built up in two applications and fired as given below. The first application was fairly thin. Fired cores were sectioned, polished with 120 and 400 grit sandpaper. Polished cross-sections were studied using an optical microscope at magnifications of 50× and 200×. Cores were found to be fully dense. Only occasionally pores smaller than 30 um were observed. Some of the copings were built up to full crowns using OPC® 3G™ porcelain available from Jeneric/Pentron Inc., Wallingford, Conn. and found to be more than adequate in aesthetics and function. Additionally, the powder of composition 26 was wet-condensed into bars. The bars were fired and polished as per ISO-6872. Three-point bend testing was conducted on ten bars and the flexure strength was measured to be 241±25.

TABLE 4

| composition | 24 | | 25 | | 26 (= 11 from Table 3) | |
|---|---|---|---|---|---|---|
| oxide | Wt % | Mole % | Wt % | Mole % | Wt % | Mole % |
| SiO$_2$ | 68.7 | 64.08 | 70.6 | 64.73 | 68.8 | 63.68 |
| B$_2$O$_3$ | — | — | 0.9 | 0.71 | 1.2 | 1.00 |
| Al$_2$O$_3$ | 4.8 | 2.64 | 4.8 | 2.59 | 4.8 | 2.62 |
| ZnO | 0 | 0.00 | 0 | 0.0 | 0 | 0.00 |
| MgO | 0 | 0.00 | 0 | 0.0 | 0 | 0.00 |
| SrO | 0 | 0.00 | 0 | 0.0 | 0 | 0.00 |
| CaO | 1.0 | 1.0 | 0.5 | 0.49 | 1.0 | 0.99 |
| BaO | 2.8 | 1.02 | 1.4 | 0.50 | 2.8 | 1.02 |
| Li$_2$O | 14.4 | 27.01 | 14.7 | 27.10 | 14.4 | 26.80 |
| K$_2$O | 2.2 | 1.31 | 2.1 | 1.23 | 2.2 | 1.30 |
| Na$_2$O | 1.5 | 1.36 | 1.4 | 1.24 | 1.4 | 1.30 |
| ZrO$_2$ | 0 | 0.00 | 0 | 0.00 | 0 | 0.00 |
| TiO$_2$ | 0 | 0.00 | 0 | 0.00 | 0 | 0.00 |
| P$_2$O$_5$ | 3.3 | 1.30 | 3.6 | 1.40 | 3.3 | 1.29 |
| Tb$_4$O$_7$ | 0.7 | 0.05 | 0 | 0.00 | 0 | 0.00 |
| CeO$_2$ | 0.7 | 0.23 | 0 | 0.00 | 0 | 0.00 |
| Molar Ratio of (Na$_2$O + K$_2$O + CaO + SrO + BaO)/(Al$_2$O$_3$ + ZnO) | 1.78 | | 1.34 | | 1.76 | |
| Firing Temperature | 890° C. × 1 min hold | | 890° C. × 1 min hold | | 890° C. × 1 min hold | |

The glass-ceramics of the present invention have the capability to be used to fabricate dental articles using powder application techniques, pressing techniques or machining techniques to provide single or multi-unit dental restorations at temperatures below about 950° C. using already existing, commercially available equipment such as the Autopress available from Jeneric/Pentron, Wallingford, Conn. Pressability or ability to flow and be pressed into complex shapes of dental restorations at these temperatures is achieved due to the presence of a sufficient amount of the residual glass in the resulting glass-ceramic, in the range of about 15%–60% by volume. The glass-ceramics of the present invention have the capability to be shaded by admixing pigments to the glass-ceramic powder by methods commonly used for dental porcelains.

As will be appreciated, the present invention provides a simple and effective method for producing lithium disilicate glass-ceramic compositions and dental restorations therefrom. While various descriptions of the present invention are described above, it should be understood that the various features can be used singly or in any combination thereof. Therefore, this invention is not to be limited to only the specifically preferred embodiments depicted herein.

Further, it should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. A dental restoration comprising in weight percent:
   about 62 to about 85% SiO$_2$;
   about 1.5 to about 10% Al$_2$O$_3$;

about 8 to about 19% $Li_2O$;
about 2.5 to about 7% $K_2O$;
about 0.5 to about 12% $P_2O_5$;
up to about 7% CaO;
up to about 5% ZnO;
up to about 1% SrO;
up to about 5% $Na_2O$;
up to about 7% BaO; and
wherein the molar ratio of $(Na_2O+K_2O+CaO+SrO+BaO)/(Al_2O_3+ZnO) \geq 1.3$.

2. The dental restoration of claim 1 manufactured from a glass-ceramic that is pressable.

3. The dental restoration of claim 1 further comprising in weight percent:
up to about 4.9% $B_2O_3$;
up to about 1.5% F;
up to about 2% MgO;
up to about 5% $Cs_2O$;
up to about 2% $TiO_2$;
up to about 3% $ZrO_2$;
up to about 1% $SnO_2$;
up to about 1% $Sb_2O_3$;
up to about 3% $Y_2O_3$;
up to about 1% $CeO_2$;
up to about 1% $Eu_2O_3$;
up to about 1% $Tb_4O_7$;
up to about 2% $Nb_2O_5$; and
up to about 2% $Ta_2O_5$.

4. The dental restoration of claim 1 formed into a component selected from orthodontic appliances, bridges, space maintainers, tooth replacement appliances, splints, crowns, partial crowns, dentures, posts, teeth, jackets, inlays, onlays, facing, veneers, facets, implants, abutments, cylinders, and connector.

5. The dental restoration of claim 1 manufactured from a blank of glass ceramic material.

6. The dental restoration of claim 1 manufactured from a glass-ceramic formable powder.

7. A glass-ceramic composition comprising in weight percent:
about 64 to about 70% $SiO_2$;
about 1.5 to about 6 $Al_2O_3$;
about 10 to about 15% $Li_2O$;
about 2.5 to about 5% $K_2O$;
about 2 to about 7% $P_2O_5$;
up to about 7% BaO;
up to about 1% SrO;
up to about 2% ZnO;
up to about 0.9% CaO;
up to about 3% $Na_2O$; and
wherein the molar ratio of $(Na_2O+K_2O+CaO+SrO+BaO)/(Al_2O_3+ZnO) \geq 1.3$.

8. The glass-ceramic composition of claim 7 whereby the glass-ceramic is pressable.

9. The glass-ceramic composition of claim 7 further comprising in weight percent:
up to about 1.5% F;
up to about 5% $Cs_2O$;
up to about 2.7% $B_2O_3$;
up to about 2% MgO;
up to about 2% $TiO_2$;
up to about 3% $ZrO_2$;
up to about 1% $SnO_2$;
up to about 1% $Sb_2O_3$;
up to about 3% $Y_2O_3$;
up to about 1% $CeO_2$;
up to about 1% $Eu_2O_3$;
up to about 1% $Tb_4O_7$;
up to about 2% $Nb_2O_5$; and
up to about 2% $Ta_2O_5$.

10. A dental restoration comprising the glass-ceramic of claim 7.

11. A glass-ceramic composition comprising in weight percent:
about 62 to about 85% $SiO_2$;
about 5.1 to about 10 $Al_2O_3$;
about 8 to about 19% $Li_2O$;
about 0.5 to about 12% $P_2O_5$;
up to about 5% $Na_2O$;
up to about 7% $K_2O$;
up to about 7% CaO;
up to about 1% SrO;
up to about 7% BaO;
up to about 5% ZnO; and
wherein the molar ratio of $(Na2O+K_2O+CaO+SrO+BaO)/(Al_2O_3+ZnO) \geq 1.3$.

12. The glass-ceramic composition of claim 11 whereby the glass-ceramic is pressable.

13. The glass-ceramic composition of claim 11 further comprising in weight percent:
up to about 1.5% F;
up to about 5% $Cs_2O$;
up to about 4.9% $B_2O_3$;
up to about 2% MgO;
up to about 2% $TiO_2$;
up to about 3% $ZrO_2$;
up to about 1% $SnO_2$;
up to about 1% $Sb_2O_3$;
up to about 3% $Y_2O_3$;
up to about 1% $CeO_2$;
up to about 1% $Eu_2O_3$;
up to about 1% $Tb_4O_7$;
up to about 2% $Nb_2O_5$; and
up to about 2% $Ta_2O_5$.

14. A dental restoration comprising the glass-ceramic of claim 11.

15. A glass-ceramic composition comprising in weight percent:
about 64 to about 70% $SiO_2$;
about 5.2 to about 9 $Al_2O_3$;
about 10 to about 15% $Li_2O$;
about 2 to about 7% $P_2O_5$;
up to about 3% $Na_2O$;
up to about 5% $K_2O$;
up to about 0.9% CaO;
up to about 1% SrO;
up to about 7% BaO;
up to about 2% ZnO; and
wherein the molar ratio of $(Na_2O+K_2O+CaO+SrO+BaO)/(Al_2O_3+ZnO) \geq 1.3$.

16. The glass-ceramic composition of claim 15 whereby the glass-ceramic is pressable.

17. The glass-ceramic composition of claim 15 further comprising in weight percent:
up to about 1.5% F;
up to about 5% $Cs_2O$;
up to about 2.7% $B_2O_3$;
up to about 2% MgO;
up to about 2% $TiO_2$;
up to about 3% $ZrO_2$;
up to about 1% $SnO_2$;
up to about 1% $Sb_2O_3$;
up to about 3% $Y_2O_3$;
up to about 1% $CeO_2$;
up to about 1% $Eu_2O_3$;
up to about 1% $Tb_4O_7$;
up to about 2% $Nb_2O_5$; and
up to about 2% $Ta_2O_5$.

18. A dental restoration comprising the glass-ceramic of claim 15.

19. A glass-ceramic composition comprising in weight percent:
about 64 to about 70% $SiO_2$;
about 1.5 to about 6 $Al_2O_3$;
about 10 to about 15% $Li_2O$;
about 2 to about 7% $P_2O_5$;
about 2.2 to about 5% $K_2O$;
about 0.5 to about 3% $Na_2O$;
about 0.5 to about 3% $B_2O_3$;
up to about 0.9% CaO;
up to about 1% SrO;
up to about 7% BaO;
wherein the molar ratio of $(Na_2O+K_2O+CaO+SrO+BaO)/(Al_2O_3) \geq 1.3$.

20. The glass-ceramic composition of claims 19 whereby the glass-ceramic is pressable.

21. The glass-ceramic composition of claims 19 further comprising in weight percent:
up to about 1.5% F;
up to about 5% $Cs_2O$;
up to about 2% $TiO_2$;
up to about 3% $ZrO_2$;
up to about 1% $SnO_2$;
up to about 1% $Sb_2O_3$;
up to about 3% $Y_2O_3$;
up to about 1% $CeO_2$;
up to about 1% $Eu_2O_3$;
up to about 1% $Tb_4O_7$;
up to about 2% $Nb_2O_5$; and
up to about 2% $Ta_2O_5$.

22. A dental restoration comprising the glass-ceramic of claim 19.

23. A glass-ceramic composition comprising in weight percent:
about 62 to about 76% $SiO_2$;
about 1.5 to about 10 $Al_2O_3$;
about 8 to about 19% $Li_2O$;
about 0.3 to about 7% $P_2O_5$;
about 0.5 to about 8% $Ta_2O_5$;
up to about 5% $Na_2O$;
up to about 7% $K_2O$;
up to about 7% CaO;
up to about 1% SrO;
up to about 7% BaO;
up to about 5% ZnO;
wherein the molar ratio of $(Na_2O+K_2O+CaO+SrO+BaO)/(ZnO+Al_2O_3) \geq 1.3$.

24. The glass-ceramic composition of claim 23 whereby the glass-ceramic is pressable.

25. The glass-ceramic composition of claim 23 further comprising in weight percent:
up to about 5% $B_2O_3$.
up to about 1.5% F;
up to about 2% MgO;
up to about 5% $Cs_2O$;
up to about 2% $TiO_2$;
up to about 3% $ZrO_2$;
up to about 1% $SnO_2$;
up to about 1% $Sb_2O_3$;
up to about 3% $Y_2O_3$;
up to about 1% $CeO_2$;
up to about 1% $Eu_2O_3$;
up to about 1% $Tb_4O_7$; and
up to about 2% $Nb_2O_5$.

26. A dental restoration comprising the glass-ceramic of claim 23.

27. A method of making a lithium disilicate dental restoration comprising:
melting a starting glass composition at temperatures within the range of about 1200 to about 1600° C.;
quenching the glass melt;
subjecting the quenched glass to one or more heat treatments in the temperature range of from about 400° to about 1100° C. to convert the glass into a glass-ceramic;
comminuting the glass ceramic to a powder;
forming the powder onto a die to form a dental restoration; and
sintering the formed dental restoration.

28. The method of claim 27 wherein the glass-ceramic composition comprises:
about 62 to about 85% $SiO_2$;
about 1.5 to about 10% $Al_2O_3$;
about 8 to about 19% Li2O;
about 0.5 to about 12% $P_2O_5$;
up to about 7% CaO;
up to about 5% ZnO;
up to about 1% SrO;
up to about 5% $Na_2O$;
up to about 7% BaO; and
wherein the molar ratio of $(Na_2O+K_2O+CaO+SrO+BaO)/(Al_2O_3+ZnO) \geq 1.3$.

29. The method of claim 27 wherein the glass-ceramic composition comprises:
about 64 to about 70% $SiO_2$;
about 1.5 to about 6 $Al_2O_3$;
about 10 to about 15% $Li_2O$;
about 2.5 to about 5% $K_2O$;
about 2 to about 7% $P_2O_5$;

up to about 7% BaO;
up to about 1% SrO;
up to about 2% ZnO;
up to about 0.9% CaO;
up to about 3% Na$_2$O; and
wherein the molar ratio of (Na$_2$O+K$_2$O+CaO+SrO+BaO)/(Al$_2$O$_3$+ZnO)≧1.3.

30. The method of claim 27 wherein the glass-ceramic composition comprises:
about 62 to about 85% SiO$_2$;
about 5.1 to about 10 Al$_2$O$_3$;
about 8 to about 19% Li$_2$O;
about 0.5 to about 12 % P$_2$O$_5$;
up to about 5% Na$_2$O;
up to about 7% K$_2$O;
up to about 7% CaO;
up to about 1% SrO;
up to about 7% BaO;
up to about 5% ZnO; and
wherein the molar ratio of (Na$_2$O+K$_2$O+CaO+SrO+BaO)/(Al$_2$O$_3$+ZnO)≧1.3.

31. The method of claim 27 wherein the glass-ceramic composition comprises:
about 64 to about 70% SiO$_2$;
about 5.2 to about 9 Al$_2$O$_3$;
about 10 to about 15% Li$_2$O;
about 2 to about 7% P$_2$O$_5$;
up to about 3% Na$_2$O;
up to about 5% K$_2$0;
up to about 0.9% CaO;
up to about 1% SrO;
up to about 7% BaO;
up to about 2% ZnO; and
wherein the molar ratio of (Na$_2$O+K$_2$O+CaO+SrO+BaO)/(Al$_2$O$_3$+ZnO)≧1.3.

32. The method of claim 27 wherein the glass-ceramic composition comprises:
about 64 to about 70% SiO$_2$;
about 1.5 to about 6 Al$_2$O$_3$;
about 10 to about 15% Li$_2$O;
about 2 to about 7% P$_2$O$_5$;
about 2.2 to about 5% K$_2$O;
about 0.5 to about 3% Na$_2$O;
about 0.5 to about 3% B$_2$O$_3$;
up to about 0.9% CaO;
up to about 1 % SrO;
up to about 7% BaO; and
wherein the molar ratio of (Na$_2$O+K$_2$O+CaO+SrO+BaO)/(Al$_2$O$_3$)≧1.3.

33. The method of claim 27 wherein the glass-ceramic composition comprises:
about 62 to about 76% SiO$_2$;
about 1.5 to about 10 Al$_2$O$_3$;
about 8 to about 19% Li$_2$O;
about 0.3 to about 7% P$_2$O$_5$;
about 0.5 to about 8% Ta$_2$O$_5$;
up to about 5% Na$_2$O;
up to about 7% K$_2$O;
up to about 7% CaO;
up to about 1% SrO;
up to about 7% BaO;
up to about 5% ZnO; and
wherein the molar ratio of (Na$_2$O+K$_2$O+CaO+SrO+BaO)/(ZnO+Al$_2$O$_3$)≧1.3.

* * * * *